United States Patent [19]

Lesher et al.

[11] 4,298,609

[45] Nov. 3, 1981

[54] 4,5-DIHYDRO-6-(4-PYRIDINYL)-3-PYRIDAZINOL AND SALTS, THEIR PREPARATION AND USE AS BLOOD PRESSURE LOWERING AGENTS

[75] Inventors: George Y. Lesher, Schodack; William B. Dickinson, Albany, both of N.Y.

[73] Assignee: Sterling Drug Inc., New York, N.Y.

[21] Appl. No.: 71,064

[22] Filed: Aug. 30, 1979

[51] Int. Cl.³ .................... A61K 31/50; C07D 237/22
[52] U.S. Cl. ..................................... 424/250; 544/238
[58] Field of Search ......................... 544/238; 424/250

[56] References Cited

FOREIGN PATENT DOCUMENTS 52-19987  7/1977  Japan .

OTHER PUBLICATIONS

McEvoy et al. J. Org. Chem. 38, 4044–4048 (1978).
McEvoy et al. J. Med. Chem. 17, 281–286, (1974).
Curran et al. J. Medicinal Chemistry 17, 273–281, (1974).

*Primary Examiner*—Anton H. Sutto
*Attorney, Agent, or Firm*—Robert K. Bair; B. Woodrow Wyatt

[57] ABSTRACT

4,5-Dihydro-6-(4-pyridinyl)-3-pyridazinol or pharmaceutically-acceptable acid-addition salt thereof is useful as a blood pressure lowering agent. 4,5-Dihydro-6-(4-pyridinyl)-3-pyridazinol is prepared by reacting γ-oxo-γ-(4-pyridinyl)butyronitrile with a hydrazine salt of a strong inorganic or organic sulfonic acid. Said 4,5-dihydro-6-(4-pyridinyl)-3-pyridazinol or pharmaceutically-acceptable salt thereof is shown as the active ingredient in pharmaceutical compositions for lowering blood pressure and in the method for lowering blood pressure in a patient having elevated blood pressure.

7 Claims, No Drawings

4,5-DIHYDRO-6-(4-PYRIDINYL)-3-PYRIDAZINOL AND SALTS, THEIR PREPARATION AND USE AS BLOOD PRESSURE LOWERING AGENTS

CROSS-REFERENCE TO RELATED APPLICATION

The instantly claimed 4,5-dihydro-6-(4-pyridinyl)-3-pyridazinol, a blood pressure lowering agent, also is useful as an intermediate in the preparation of 6-(4-pyridinyl)-3-pyridazinol which is disclosed and claimed in copending application Ser. No. 71,065, filed on Aug. 30, 1979 and now abandoned in favor of its copending continuation-in-part application Ser. No. 144,576, filed Apr. 28, 1980.

BACKGROUND OF THE INVENTION (a) Field of the Invention

This invention relates to 4,5-dihydro-6-substituted-3-pyridazinols, their use as blood pressure lowering agents, and their preparation.

(b) Description of the Prior Art

The Yoshitomi Pharmaceutical Ind., Ltd. Japanese Patent Application Disclosure No. 19,987/79, published Feb. 15, 1979 and based on Application No. 85,192/77, filed July 15, 1977, discloses, inter alia, the preparation of 4,5-dihydro-6-(4-pyridinyl)-3(2H)-pyridazinone by refluxing for two hours an ethanolic solution of 3-(isonicotinoyl)propanoic acid [same as γ-oxo-γ-(4-pyridinyl)butyric acid] and hydrazine hydrate. 4,5-Dihydro-6-(4-pyridinyl)-3(2H)-pyridazinone and closely related 4,5-dihydro-6-(4- or 3- or 2-pyridinyl)-5-R-3(2H)-pyridazinones, where R is H or lower alkyl, are said (page 2 of English translation) to be "useful not only as medicines such as hypotensive and antithrombus agents because they have pharmacological actions such as hypotensive, blood platelet coagulation-inhibitory and membrane-stabilizing actions, but also as intermediates for the synthesis of such medicines".

McEvoy and Allen [J. Org. Chem. 38, 4044-48 (1978); J. Med. Chem. 17, 281-286 (1974)] show a method for preparing 3-(substituted-benzoyl)-3-substituted-alkanoic acids and their reaction with hydrazine to prepare 6-(substituted-phenyl)-5-substituted-4,5-dihydro-3(2H)-pyridazinones, hypotensive agents.

Curran and Ross [J. Med. Chem. 17, 273-281 (1974)] show the preparation of 6-phenyl-4,5-dihydro-3(2H)-pyridazinones, hypotensive agents, by refluxing the requisite 3-benzoylproponic acid with hydrazine hydrate in ethanol.

SUMMARY OF THE INVENTION

In its composition aspect, the invention resides in the compound, 4,5-dihydro-6-(4-pyridinyl)-3-pyridazinol or salt, useful as a blood pressure lowering agent.

In a process aspect the invention comprises reacting γ-oxo-γ-(4-pyridinyl)butyronitrile with a hydrazine salt of a strong acid.

Another composition aspect of the invention relates to a pharmaceutical composition for lowering blood pressure in a patient having elevated blood pressure which comprises a pharmaceutically-acceptable carrier and, as the active ingredient thereof, 4,5-dihydro-6-(4-pyridinyl)-3-pyridazinol or salt.

In a method aspect, the invention relates to a method for lowering blood pressure in a patient having elevated blood pressure which comprises administering to said patient a blood pressure lowering amount of 4,5-dihydro-6-(4-pyridinyl)-3-pyridazinol or salt.

DETAILED DESCRIPTION INCLUSIVE OF PREFERRED EMBODIMENTS

In a composition aspect the invention resides in 4,5-dihydro-6-(4-pyridinyl)-3-pyridazinol or pharmaceutically-acceptable acid-addition salt thereof. These compounds are useful as blood pressure lowering agents, as determined by standard pharmacological evaluation procedures. They are also useful as intermediates in the preparation of 6-(4-pyridinyl)-3-pyridazinol, a cardiotonic agent, as disclosed and claimed in copending application Ser. No. 71,065, filed Aug. 30, 1979 and now abandoned in favor of its copending continuation-in-part application Ser. No. 144,576, filed Apr. 28, 1980.

In a process aspect the invention resides in the process of producing 4,5-dihydro-6-(4-pyridinyl)-3-pyridazinol which comprises reacting γ-oxo-γ-(4-pyridinyl)butyronitrile with a hydrazine salt of a strong inorganic or organic sulfonic acid to produce 4,5-dihydro-6-(4-pyridinyl)-3-pyridazinol. In a preferred embodiment, this process is run using hydrazine sulfate in an aqueous lower-alkanol solvent, preferably aqueous ethanol.

Another composition aspect of the invention resides in a pharmaceutical composition for lowering blood pressure which comprises a pharmaceutically-acceptable carrier and, as the active component thereof, a blood pressure lowering effective amount of 4,5-dihydro-6-(4-pyridinyl)-3-pyridazinol or pharmaceutically-acceptable acid-addition salt thereof.

Another method aspect of the invention resides in the method for lowering blood pressure in a patient having elevated blood pressure which comprises administering orally or parenterally in a solid or liquid dosage form to such patient a blood pressure lowering effective amount of 4,5-dihydro-6-(4-pyridinyl)-3-pyridazinol or pharmaceutically-acceptable acid-addition salt thereof.

The 4,5-dihydro-6-(4-pyridinyl)-3-pyridazinol is useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial blood pressure lowering properties inherent in the free base are not vitiated by side effects ascribable to the anions. In practicing the invention, it was convenient to utilize the compound of the invention in its free base form. However, appropriate pharmaceutically-acceptable salts within the scope of the invention are those derived from mineral acids such as sulfuric acid, phosphoric acid, hydrochloric acid and sulfamic acid; and organic acids such as methanesulfonic acid, lactic acid, acetic acid, citric acid, tartaric acid, ethanesulfonic acid, benzenesulfonic acid, p-toluenesulfonic acid, cyclohexylsulfamic acid, quinic acid, and the like, giving the sulfate, phosphate, hydrochloride, sulfamate, methanesulfonate, lactate, acetate, citrate, tartrate, ethanesulfonate, benzenesulfonate, p-toluenesulfonate, cyclohexylsulfamate and quinate, respectively.

The acid-addition salts of said basic compound are prepared either by dissolving the free base in an aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base even if the particular salt per se is desired only as an intermediate product as for example when the salt is formed only for purposes of purification or identification, or when it is used as an intermediate in preparing a pharmaceutically-acceptable salt by anion exchange procedures.

The molecular structure of 4,5-dihydro-6-(4-pyridinyl)-3-pyridazinol was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The reaction of γ-oxo-γ-(4-pyridinyl)butyronitrile with a hydrazine salt of a strong inorganic or organic sulfonic acid to produce 4,5-dihydro-6-(4-pyridinyl)-3-pyridazinol is carried out by heating the reactants at about 65°–120° C. in a suitable solvent, preferably at about 80°–100° C. in a mixture of water and a lower alkanol. The reaction is preferably run by refluxing γ-oxo-γ-(4-pyridinyl)butyronitrile with hydrazine sulfate in aqueous ethanol. Other hydrazine salts usable are hydrazine dihydrochloride, hydrazine dimethanesulfonate, and the like salts derived from phosphoric acid, ethanesulfonic acid, benzenesulfonic acid, and the like acids. Other lower-alkanols useful as solvents are methanol, n-propanol, 2-propanol, n-butanol, 2-butanol and 2-methyl-n-propanol.

The intermediate γ-oxo-γ-(4-pyridinyl)butyronitrile is a known compound [Stetter et al., Chem. Ber. 107, 210 (1974)].

The following examples will further illustrate the invention without, however, limiting it thereto.

EXAMPLE 1

4,5-Dihydro-6-(4-pyridinyl)-3-pyridazinol

A mixture containing a 2.4 g. of γ-oxo-γ-(4-pyridinyl)butyronitrile, 1.96 g. of hydrazine sulfate, 100 ml. of absolute ethanol and 100 ml. of water was refluxed with stirring overnight (about 15 hours. The reaction mixture was heated in vacuo to remove the solvent mixture. The remaining residue was taken up in water and filtered. The filtrate was neutralized with 10% aqueous sodium bicarbonate solution and a yellow solid separated. The solid was collected, washed with water, dried in vacuo over $P_2O_5$ for four hours. Its nuclear magnetic resonance (nmr) and mass spectra were found to be consistent with that of the desired product but showed traces of impurities. The solid was then recrystallized from absolute ethanol, dried in vacuo over $P_2O_5$ overnight to yield, as golden crystals, 0.9 g. of 4,5-dihydro-6-(4-pyridinyl)-3-pyridazinol, m.p. 185°–187° C. Its nmr and mass spectra were consistent with the assigned structure.

The above reaction is run by using a molar equivalent quantity of hydrazine dihydrochloride or hydrazine di(methanesulfonate) in place of hydrazine sulfate.

Acid-addition salts of 4,5-dihydro-6-(4-pyridinyl)-3-pyridazinol are conveniently prepared by adding to a mixture of 1 g. of 4,5-dihydro-6-(4-pyridinyl)-3-pyridazinol in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., dihydrochloride, dimethanesulfonate, sulfate, respectively. Also, the mono-lactate or monohydrochloride acid-addition salt is conviently prepared in aqueous solution by adding to water with stirring molar equivalent quantities each of 4,5-dihydro-6-(4-pyridinyl)-3-pyridazinol and lactic acid or hydrochloric acid, respectively.

EXAMPLE 2

A 2 liter 3-necked round bottom flask was equipped with a mechanical stirrer, a reflux condenser and a dropping funnel. Into the flask was placed 750 ml. of acetic acid and 16.3 g. of 4,5-dihydro-6-(4-pyridinyl)-3-pyridazinol. The mixture was heated on a steam bath for about 20 minutes and then a solution containing 50 ml. of bromine and 150 ml. of acetic acid was initially added dropwise. The first 50 ml. of solution was added over a period of about 20 minutes whereupon solid began precipitating. The rest of the bromine solution was then added all at once followed by the addition of 60 ml. more of bromine. Most of the solid redissolved and the resulting mixture was heated with stirring on a steam bath for 6 hours and then allowed to stand at room temperature over the weekend (about 65 hours). A small amount of crystalline solid was filtered off and the filtrate was heated in vacuo to remove the solvent. The remaining residue was treated with 500 ml. of boiling water whereupon most of the residue dissolved. Sodium bisulfite was added to the hot mixture until bubbling of sulphur dioxide ceased. The mixture was made weakly basic to litmus paper by adding sodium bicarbonate. The solid that separated was collected, recrystallized from isopropyl alcohol and dried in a vacuum oven over $P_2O_5$ at 45° C. for seventeen hours to produce 6.0 g. of 6-(4-pyridinyl)-3-pyridazinol hydrate (6:1), m.p. 222°–224° C. Its nmr and mass spectra were consistent with the assigned structure.

Acid-addition salts of 6-(4-pyridinyl)-3-pyridazinol are conveniently prepared by adding to a mixture of 1 g. of 6-(4-pyridinyl)-3-pyridazinol in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., dihydrochloride, dimethanesulfonate, sulfate, respectively. Also, the monolactate or monohydrochloride acid-addition salt of 6-(4-pyridinyl)-3-pyridazinol is conveniently prepared in aqueous solution by adding to water with stirring molar equivalent quantities each of 6-(4-pyridinyl)-3-pyridazinol and lactic acid or hydrochloric acid, respectively.

The usefulness of 4,5-dihydro-6-(4-pyridinyl)-3-pyridazinol or salt as a blood pressure lowering agent is demonstrated by its effectiveness in standard pharmacological test procedures, for example, in causing a reduction in systolic blood pressure measured according to the method of H. Kersten et al., J. Lab. and Clin. Med. 32, 1090 (1947) following a single oral medication in the unanesthetized spontaneous hypertensive rat described by Okamato et al., Japan Circulation J. 27, 282 (1963).

4,5-Dihydro-6-(4-pyridinyl)-3-pyridazinol when tested in the spontaneously hypertensive rat by the standard method noted above was found to have an oral $AHD_{40}$ of 40 mg/kg, the $AHD_{40}$ here being defined as the single oral dose that lowers systolic blood pressure by 40 mm Hg at both 2 and 6 hours after administration of the compound.

The present invention includes within its scope a pharmaceutical composition for lowering blood pressure which comprises a pharmaceutically-acceptable carrier and, as the active component thereof, a blood pressure lowering effective amount of 4,5-dihydro-6-(4-pyridinyl)-3-pyridazinol or pharmaceutically-acceptable acid-addition salt thereof. The invention also includes within its scope the method for lowering blood pressure in a patient having elevated blood pressure which comprises administering orally or parenterally in solid or liquid dosage form to such patient a blood pressure lowering effective amount of said 4,5-dihydro-6-(4-pyridinyl)-3-pyridazinol or pharmaceutically-acceptable acid-addition salt thereof. In clinical practice said compound or salt thereof will normally be administered orally or parentally in a wide variety of dosage forms.

Solid compositions for oral administration include compressed tablets, pills, powders and granules. In such solid compositions, at least one of the active compounds is admixed with at least one inert dilutent such as starch, calcium carbonate, sucrose or lactose. These compositions may also contain additional substances other than inert diluents, e.g., lubricating agents, such magnesium steaate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavouring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in the said composition and method for lowering blood pressure may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. The method for lowering blood pressure in a patient having elevated blood pressure which comprises administering orally or parenterally in a solid or liquid dosage form to such patient a blood pressure lowering effective amount of 4,5-dihydro-6-(4-pyridinyl)-3-pyridazinol or pharmaceutically-acceptable acid-addition salt thereof.

2. 4,5-Dihydro-6-(4-pyridinyl)-3-pyridazinol or pharmaceutically-acceptable acid-addition salt thereof.

3. 4,5-Dihydro-6-(4-pyridinyl)-3-pyridazinol.

4. A pharmaceutical composition for lowering blood pressure, which comprises a pharmaceutically-acceptable inert carrier and, as the active component thereof, a blood pressure lowering effective amount of 4,5-dihydro-6-(4-pyridinyl)-3-pyridazinol or pharmaceutically-acceptable acid-addition salt thereof.

5. A composition according to claim 4 where the active component is 4,5-dihydro-6-(4-pyridinyl)-3-pyridazinol.

6. The process which comprises heating at about 65°–120° C. γ-oxo-γ-(4-pyridinyl)butyronitrile with a hydrazine salt of a strong inorganic or organic sulfonic acid to produce 4,5-dihydro-6-(4-pyridinyl)-3-pyridazinol.

7. The process according to claim 6 where the reaction is run by refluxing γ-oxo-γ-(4-pyridinyl)butyronitrile with hydrazine sulfate in aqueous ethanol.

* * * * *